(12) United States Patent
Ishikawa et al.

(10) Patent No.: US 11,983,305 B2
(45) Date of Patent: May 14, 2024

(54) CONTENT PRESENTATION SYSTEM, CONTENT PRESENTATION DEVICE, AND CONTENT PRESENTATION METHOD

(71) Applicant: SONY GROUP CORPORATION, Tokyo (JP)

(72) Inventors: Takanori Ishikawa, Tokyo (JP); Ryo Sasaki, Tokyo (JP); Yuta Aoki, Tokyo (JP)

(73) Assignee: Sony Group Corporation, Tokyo (JP)

( * ) Notice: Subject to any disclaimer, the term of this patent is extended or adjusted under 35 U.S.C. 154(b) by 0 days.

(21) Appl. No.: 18/001,760

(22) PCT Filed: May 19, 2021

(86) PCT No.: PCT/JP2021/018923
§ 371 (c)(1),
(2) Date: Dec. 14, 2022

(87) PCT Pub. No.: WO2021/261123
PCT Pub. Date: Dec. 30, 2021

(65) Prior Publication Data
US 2023/0244297 A1 Aug. 3, 2023

(30) Foreign Application Priority Data

Jun. 25, 2020 (JP) ................................. 2020-109359

(51) Int. Cl.
*G06F 3/01* (2006.01)
(52) U.S. Cl.
CPC ........ *G06F 3/011* (2013.01); *G06F 2203/011* (2013.01)

(58) Field of Classification Search
None
See application file for complete search history.

(56) References Cited

U.S. PATENT DOCUMENTS

2018/0336276 A1    11/2018  Fukino et al.
2019/0187870 A1*    6/2019  Bostick ............... G06V 40/174

FOREIGN PATENT DOCUMENTS

EP    3287075 A1    2/2018
JP    2007-328464   12/2007
(Continued)

OTHER PUBLICATIONS

English machine translation of Japanese patent publication JP 2008-204193 (Year: 2008).*

(Continued)

*Primary Examiner* — Nicholas J Lee
(74) *Attorney, Agent, or Firm* — Sheridan Ross PC

(57) ABSTRACT

A content presentation system, a content presentation device, and a content presentation method that reduce a burden on a user and present suitable contents to the user with high accuracy are provided. The present technology provides a content presentation system including a computer device that holds content information associated with emotion information indicating an emotion of a user, in which the computer device at least includes a machine learning model that, on the basis of a plurality of pieces of content information presented to the user corresponding to desired emotion information indicating emotion information desired by the user and content information selected by the user from the plurality of pieces of content information, performs machine learning so as to present the content information suitable for the emotion information.

9 Claims, 7 Drawing Sheets

(56) References Cited

FOREIGN PATENT DOCUMENTS

| JP | 2008-204193 | 9/2008 |
| JP | 2014-219937 | 11/2014 |
| JP | 2018-195043 | 12/2018 |
| JP | 2019-208576 | 12/2019 |
| WO | WO-2019017124 A1 | 1/2019 |

OTHER PUBLICATIONS

Kawashima et al., "Deep Reinforcement Learning for Recommendation System," 32nd Annual Conference of the Japanese Society for Artificial Intelligence, Jul. 6, 2018, 4 pages (with English abstract).

International Search Report and Written Opinion prepared by the Japan Patent Office dated Jun. 30, 2021, for International Application No. PCT/JP2021/018923, 2 pgs.

* cited by examiner

CONTENT PRESENTATION SYSTEM, CONTENT PRESENTATION DEVICE, AND CONTENT PRESENTATION METHOD

CROSS REFERENCE TO RELATED APPLICATIONS

This application is a national stage application under 35 U.S.C. 371 and claims the benefit of PCT Application No. PCT/JP2021/018923, having an international filing date of 19 May 2021, which designated the United States, which PCT application claimed the benefit of Japanese Patent Application No. 2020-109359, filed 25 Jun. 2020, the entire disclosures of each of which are incorporated herein by reference.

TECHNICAL FIELD

The present technology relates to a content presentation system, a content presentation device, and a content presentation method.

BACKGROUND ART

Conventionally, technology has been disclosed in which contents associated with biometric information, behavior information, attribute information, and the like related to a user are presented to the user.

For example, Patent Document 1 discloses "a preference determination system including a biometric information measurement unit that measures biometric information of a user, a behavior information measurement unit that measures behavior information of the user, an attribute information input unit that inputs attribute information of the user, a database that stores past biometric information, behavior information, attribute information, and preference items of a user in association with each other, and a preference determination unit that acquires biometric information measured by the biometric information measurement unit, behavior information measured by the behavior information measurement unit, and attribute information input by the attribute information input unit, and determines preference of the user by collating the acquired biometric information, the behavior information, and the attribute information with the database". Patent Document 1 describes technology of determining user's preference by a machine learning method and presenting recommended contents or the like to the user.

For example, Patent Document 2 discloses "a purchasing behavior management device that gives an instruction for purchasing behavior of food, the purchasing behavior management device including a basic information acquisition unit that acquires basic information that is information regarding a user, and a purchasing behavior determination unit that determines an intake state of various nutritional components of a user on the basis of basic information acquired by the basic information acquisition unit described above and determines propriety of purchasing behavior on the basis of a result of the determination, in which the basic information acquisition unit described above continuously acquires, as the basic information described above, at least biometric information of a user and purchasing behavior information indicating a content of purchasing behavior by a user". Patent Document 2 describes technology of advising a user on food purchase behavior suitable for the user.

CITATION LIST

Patent Document

Patent Document 1: Japanese Patent Application Laid-Open No. 2014-219937
Patent Document 2: Japanese Patent Application Laid-Open No. 2007-328464

SUMMARY OF THE INVENTION

Problems to be Solved by the Invention

However, for example, a machine learning model used in Patent Document 1 and the like is required to have high generalization performance. The generalization performance refers to performance in which determination can be performed appropriately and accurately even on the basis of information obtained from an unlearned user. Patent Document 1 does not disclose this generalization performance.

Furthermore, for example, in the technology disclosed in Patent Document 2 and the like, information such as things a user likes or dislikes, for example, is required to be registered. However, such information changes depending on the context. Therefore, information corresponding to various contexts, and there is an issue that a burden on a user is large.

Therefore, a main object of the present technology is to provide a content presentation system, a content presentation device, and a content presentation method that reduce a burden on a user and present suitable contents to the user with high accuracy.

Solutions to Problems

The present technology provides a content presentation system including a computer device that holds content information associated with emotion information indicating an emotion of a user, in which the computer device at least includes a machine learning model that, on the basis of a plurality of pieces of content information presented to the user corresponding to desired emotion information indicating emotion information desired by the user and content information selected by the user from the plurality of pieces of content information, performs machine learning so as to present the content information suitable for the emotion information.

The emotion information and the content information may be associated with each other on the basis of a coordinate system having elements of the emotion as coordinate axes.

The coordinate system may be a Russell's circumplex model.

Current emotion information indicating the emotion that is current of the user may be estimated on the basis of biometric information obtained from sensing information detected by a biometric sensor.

The current emotion information may be corrected on the basis of context information related to a context of the user obtained from sensing information detected by a context sensor.

An emotion estimation unit may be further included and the emotion estimation unit may perform machine learning so as to estimate the emotion information suitable for the biometric information on the basis of the biometric information.

An operation interface unit may be further included and the operation interface unit may encourage input of the desired emotion information.

The operation interface unit may present the content information corresponding to the desired emotion information and/or encourage selection of the content information.

The operation interface unit may encourage continuous or stepwise input of the desired emotion information, and the machine learning model, on the basis of a plurality of pieces of the content information presented to the user corresponding to the desired emotion information that is predetermined in a route formed by the input and content information selected by the user from the plurality of pieces of content information, may perform machine learning so as to present the content information suitable for the desired emotion information.

The operation interface unit may encourage continuous or stepwise input of the desired emotion information, and the machine learning model, on the basis of a plurality of pieces of the content information presented to the user corresponding to a shape of a route formed by the input and the desired emotion information and content information selected by the user from the plurality of pieces of content information, may perform machine learning so as to present the content information suitable for the desired emotion information.

Furthermore, the present technology provides a content presentation device that holds content information associated with emotion information indicating an emotion of a user, the content presentation device at least including a machine learning model that, on the basis of a plurality of pieces of content information presented to the user corresponding to desired emotion information indicating emotion information desired by the user and content information selected by the user from the plurality of pieces of content information, performs machine learning so as to present the content information suitable for the emotion information.

Furthermore, the present technology provides a content presentation method including a computer device that holds content information associated with emotion information indicating an emotion of a user, the content presentation method at least including, on the basis of a plurality of pieces of content information presented to the user corresponding to desired emotion information indicating emotion information desired by the user and content information selected by the user from the plurality of pieces of content information, performing machine learning so as to present the content information suitable for the emotion information by the computer device.

MODE FOR CARRYING OUT THE INVENTION

Hereinafter, preferred embodiments for carrying out the present technology will be described. The embodiments described below illustrate examples of representative embodiments of the present technology, and the scope of the present technology is not narrowly interpreted by these. Furthermore, each drawing is a schematic view, and is not necessarily strictly illustrated.

The description of the present technology will be given in the following order.

1. First Embodiment of Present Technology (Example 1 of Content Presentation System)
 (1) Outline of Present Embodiment
 (2) Emotion Model
 (3) Flowchart
 (4) Hardware Configuration
2. Second Embodiment of Present Technology (Example 2 of Content Presentation System)
3. Third Embodiment of Present Technology (Example 3 of Content Presentation System)
4. Fourth Embodiment of Present Technology (Example 4 of Content Presentation System)
5. Fifth Embodiment of Present Technology (Example 5 of Content Presentation System)
6. Sixth Embodiment of Present Technology (Content Presentation Device)
7. Seventh Embodiment of Present Technology (Content Presentation Method)

1. First Embodiment of Present Technology
(Example 1 of Content Presentation System)

(1) Outline of Present Embodiment

A content presentation system according to one embodiment of the present technology can be used, for example, for a user to control his/her emotion. An emotion refers to overall mental process, and include affect, mood, sentiment, and the like. Examples of an emotion include happiness, relaxation, lethargy, anxiety, tension, and the like.

According to the present technology, a user can control his/her own emotion. For example, a user who feels tense can feel relaxed by viewing contents such as a moving image that makes the user feel relaxed.

The content presentation system according to the one embodiment of the present technology includes a computer device that holds content information associated with emotion information indicating an emotion of a user. The computer device encourages a user to input emotion information desired by the user (desired emotion information). The computer device presents content information associated with the emotion information to the user.

The content information includes, for example, information such as a scent, temperature, and lighting in addition to a moving image, a still image, voice, music, text, and the like. Note that the scent includes, in addition to a scent that can be perceived by a human as a scent, a scent that cannot be perceived by a human as a scent but is inhaled to exert some action on a human. For example, a medical sedative to be inhaled, gas that is odorless and acts on a physical condition of a human by being inhaled, such as oxygen or carbon dioxide, or the like is also included in the scent.

Figure 1:
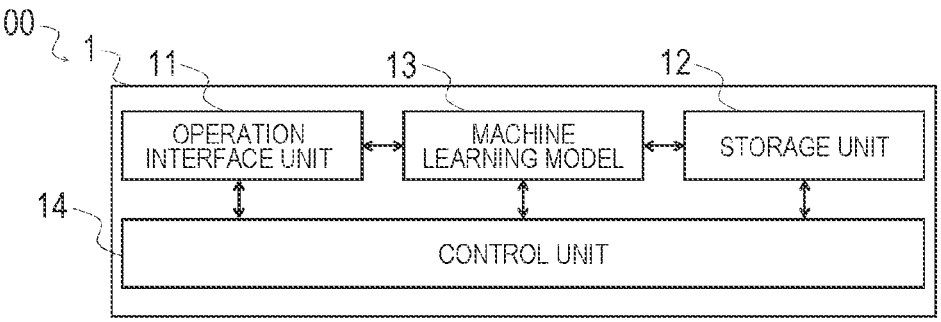
FIG. 1 is a block diagram illustrating a configuration of a content presentation system 100 according to one embodiment of the present technology.

A configuration of the content presentation system according to a first embodiment of the present technology will be described with reference to FIG. 1. FIG. 1 is a block diagram illustrating a configuration of a content presentation system 100 according to the one embodiment of the present technology. As illustrated in FIG. 1, the content presentation system 100 according to the one embodiment of the present technology includes a computer device 1. The computer device 1 can include, for example, an operation interface unit 11, a storage unit 12, a machine learning model 13, and a control unit 14.

The operation interface unit 11 encourages a user to input desired emotion information. The operation interface unit 11 can be implemented by using, for example, a touch panel or the like. The operation interface unit 11 can acquire desired emotion information by recognizing a touch operation of a user.

Alternatively, the operation interface unit 11 can be implemented by using, for example, a microphone or the like. The operation interface unit 11 can acquire desired emotion information by recognizing spoken voice of a user.

Alternatively, the operation interface unit 11 can be implemented by using, for example, a camera or the like. The operation interface unit 11 can acquire desired emotion information by performing image recognition on facial expression, a line-of-sight, and the like of a user.

The storage unit 12 holds content information associated with emotion information. In addition, the storage unit 12 may hold, for example, parameters of the machine learning model 13, history information related to user operations, attribute information related to a user, and the like.

The machine learning model 13 performs machine learning so as to present content information suitable for emotion information. More specifically, the machine learning model 13, on the basis of a plurality of pieces of content information presented to a user corresponding to the emotion information and content information selected by the user from the plurality of pieces of content information, performs machine learning so as to present the content information suitable for the emotion information.

The control unit 14 controls operation of the operation interface unit 11, the storage unit 12, and the machine learning model 13.

Here, the fact that a plurality of pieces of content information is selected will be described. In a case where the machine learning model 13 is generated, a data set in which emotion information and content information related to a plurality of people are associated with each other is used. In a case where a user to be learned by the machine learning model 13 is not included in the plurality of people, there is a possibility that the presented content information is not optimal for emotion information of the user since the characteristic of the user has not been learned.

Therefore, by presenting a plurality of pieces of content information to a user, the content presentation system 100 encourages the user to select optimal content information from the plurality of pieces of content information. The plurality of pieces of presented content information may be ranked in a suitable order for emotion information of a user. By content information being suitably selected for an emotion of a user, the machine learning model 13 can learn content information suitable for the emotion of the user. As a result, the content presentation system 100 can present content information suitable for emotion information of the user. The presented content information is customized for the user.

What the machine learning model 13 should figure out is to "present content information suitable for emotion information". Determination as to whether or not it is suitable can be made, for example, by a difference between content information presented to a user and content information selected by the user. As the difference is smaller, it can be said that contents suitable for the emotion information can be presented.

The content information presented to a user may be, for example, content information suitable for the characteristic of the user or content information that tends to be suitable for a large number of users. The former corresponds to, for example, favorite music or the like. The latter corresponds to, for example, popular music or the like. The content information is obtained from history information related to selection of content information or the like.

Note that the emotion information may be obtained from a biometric sensor, or may be obtained by the operation interface unit 11 encouraging a user to input. Details will be described below.

The machine learning model 13 performs machine learning so as to reduce this difference. The machine learning technique is not particularly specified, but for example, parameters (weighting coefficients) of a neural network that is the machine learning model 13 may be updated by reinforcement learning. The machine learning model 13 can be implemented to obtain a higher reward as the difference is smaller to perform reinforcement learning.

Alternatively, the difference may be quantified. The machine learning model 13 may update this difference by machine learning.

According to the present technology, a user only needs to select content information suitable for his/her own emotion. The user does not need to register attribute information, for example, such as his/her age, sex, and favorite food in advance. Therefore, a burden on a user is small.

According to the present technology, learning can be performed even for an unlearned user, and suitable content information is presented with high accuracy. Therefore, generalization performance of the machine learning model 13 is high.

Note that these effects are similar in other embodiments described below. Therefore, in the description of other embodiments, repeated description is omitted.

(2) Emotion Model

The association between emotion information and content information will be described with reference to FIG. 2. FIG.

2 is a conceptual diagram illustrating an example of an emotion model according to the one embodiment of the present technology.

Figure 2:
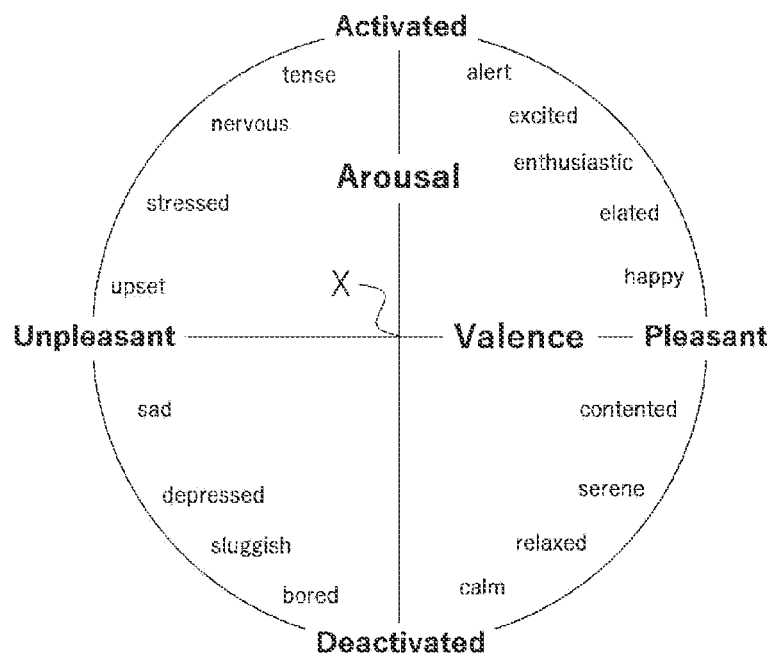
FIG. 2 is a conceptual diagram illustrating an example of an emotion model according to the one embodiment of the present technology.

FIG. 2 illustrates a coordinate system including elements of an emotion as coordinate axes. A two-dimensional coordinate system is illustrated in which the horizontal axis represents valence of "pleasant—unpleasant" and the vertical axis represents arousal. The elements of an emotion are arranged in an annular shape. For example, similar emotions such as "happy" and "contented" are arranged at positions close to each other on the annulus. On the other hand, for example, dissimilar emotions such as "happy" and "sad" are arranged at opposing positions on the annulus.

The storage unit 12 includes this coordinate system. This coordinate system is conventionally called Russell's circumplex model. This Russell's circumplex model can be used for associating emotion information with content information. A coordinate system that is not a Russell's circumplex model may be used for associating emotion information with content information. For example, Millenson's three-dimensional model or the like may be used for associating emotion information with content information.

Emotion information related to a user can be mapped to a specific coordinate with reference to the two axes. The intensity of an emotion related to a user can be indicated by a distance from an intersection X of the two axes to the specific coordinate. As a result, an emotion related to a user can be quantitatively evaluated.

Emotion information and content information are associated with coordinate information. As a result, emotion information and content information can be associated. In a case where a coordinate related to emotion information is selected, content information related to the coordinate is selected.

(3) Flowchart

Figure 3:
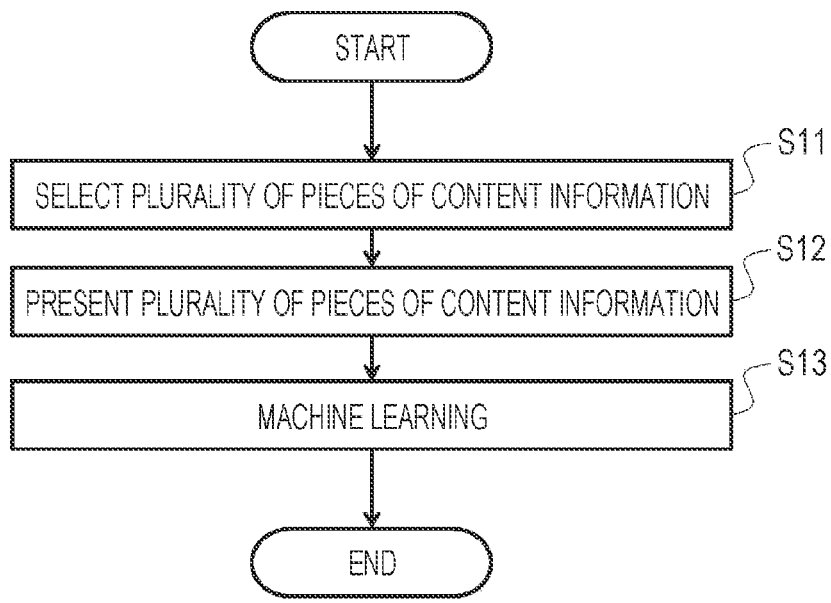
FIG. 3 is a flowchart illustrating an example of a procedure of the content presentation system 100 according to the one embodiment of the present technology.

A procedure of the content presentation system 100 will be described with reference to FIG. 3. FIG. 3 is a flowchart illustrating an example of the procedure of the content presentation system 100 according to the one embodiment of the present technology.

As illustrated in FIG. 3, first, in step S11, the machine learning model 13 selects a plurality of pieces of content information associated with obtained emotion information. The plurality of pieces of content information may be ranked according to the emotion information, for example.

In step S12, the operation interface unit 11 presents the selected plurality of pieces of content information to a user. The operation interface unit 11 encourages the user to select specific content information from the plurality of pieces of content information.

In step S13, the machine learning model 13, on the basis of the plurality of pieces of content information presented to the user and the content information selected by the user from the plurality of pieces of content information, performs machine learning so as to present the content information suitable for the emotion information.

A specific example will be described. A coordinate related to emotion information desired by a user is assumed to be (0, −10). The machine learning model 13 selects a plurality of pieces of content information associated with the coordinate or a coordinate near the coordinate (step S11). The operation interface unit 11 presents the plurality of pieces of content information to the user and encourages selection (step S12). In a case where a coordinate related to content information selected from the plurality of pieces of content information is (0, −15), the machine learning model 13 corrects the coordinate related to the content information to (0, −10) (step S13).

(4) Hardware Configuration

Figure 4:
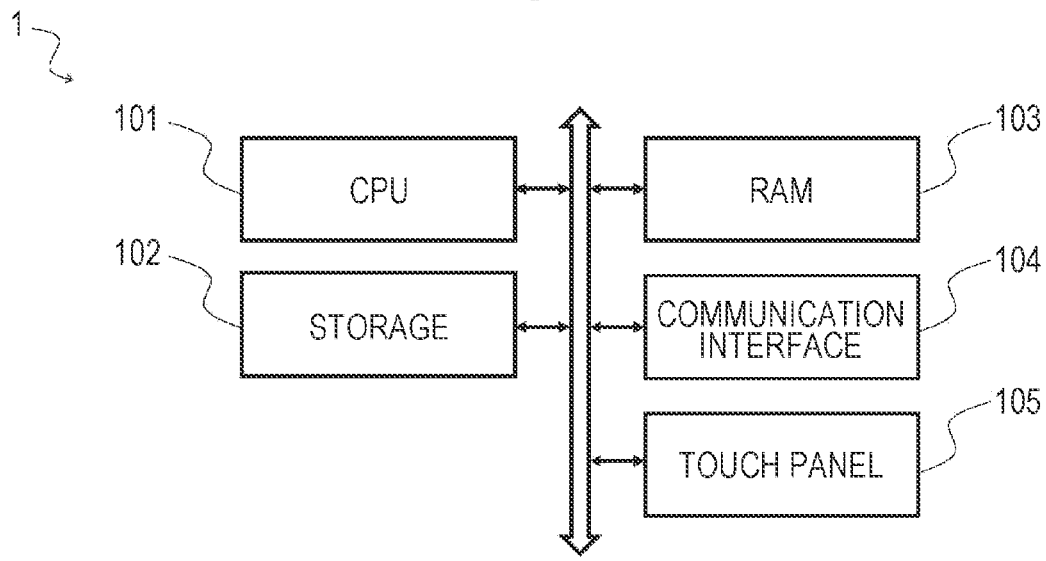
FIG. 4 is a block diagram illustrating a hardware configuration of a computer device 1 according to the one embodiment of the present technology.

A hardware configuration of the computer device 1 will be described with reference to FIG. 4. FIG. 4 is a block diagram illustrating the hardware configuration of the computer device 1 according to the one embodiment of the present technology. As illustrated in FIG. 4, the computer device 1 can include a CPU 101, a storage 102, a random access memory (RAM) 103, a communication interface 104, and a touch panel 105 as components. Each of the components is connected by, for example, a bus as a data transmission path.

The CPU 101 is implemented by, for example, a microcomputer, and controls each of the components of the computer device 1. The CPU 101 can function as, for example, the control unit 14, the machine learning model 13, and the like. The machine learning model 13 can be implemented by, for example, a program. The CPU 101 functions by reading this program.

The storage 102 stores control data and the like such as a program and operation parameters used by the CPU 101. The storage 102 can be implemented by using, for example, a hard disk drive (HDD), a solid state drive (SSD), or the like. The storage 102 can function as, for example, the storage unit 12.

The RAM 103 temporarily stores, for example, a program, and the like executed by the CPU 101.

The communication interface 104 has a function of communicating via an information communication network 3 using communication technology such as Wi-Fi, Bluetooth (registered trademark), or long term evolution (LTE) for example.

The touch panel 105 encourages a user to perform an operation by a touch operation. The touch panel 105 can function as, for example, the operation interface unit 11.

The computer device 1 may be, for example, a smartphone terminal, a tablet terminal, a mobile phone terminal, a personal digital assistant (PDA), a personal computer (PC), a portable music player, a portable game machine, or a wearable terminal (head mounted display: HMD, glasses-type HMD, watch-type terminal, band-type terminal, and the like).

A program for implementing the machine learning model 13 and the like may be stored in another computer device of the content presentation system 100 or a computer system. In this case, the content presentation system 100 can use a cloud service that provides the function of this program. Examples of the cloud service include software as a service (SaaS), infrastructure as a service (IaaS), platform as a service (PaaS), and the like.

Furthermore, the program can be stored using various types of non-transitory computer readable media and supplied to the computer. The non-transitory computer readable media include various types of tangible storage media. Examples of the non-transitory computer readable media include a magnetic recording medium (for example, flexible disk, magnetic tape, or hard disk drive), a magneto-optical recording medium (for example, magneto-optical disk), a compact disc read only memory (CD-ROM), a CD-R, a CD-R/W, and a semiconductor memory (for example, mask ROM, programmable ROM (PROM), erasable PROM (EPROM), flash ROM, or random access memory (RAM)). Furthermore, the program described above may be supplied to the computer by various types of transitory computer readable media. Examples of the transitory computer readable media include electrical signals, optical signals, and electromagnetic waves. The transitory computer readable medium can supply the program described above to the computer via a wired communication path such as an electric wire and an optical fiber or a wireless communication path.

Note that the technology used in the present embodiment can also be used in other embodiments described below. The similar applies to other embodiments.

2. Second Embodiment of Present Technology
(Example 2 of Content Presentation System)

Figure 5:
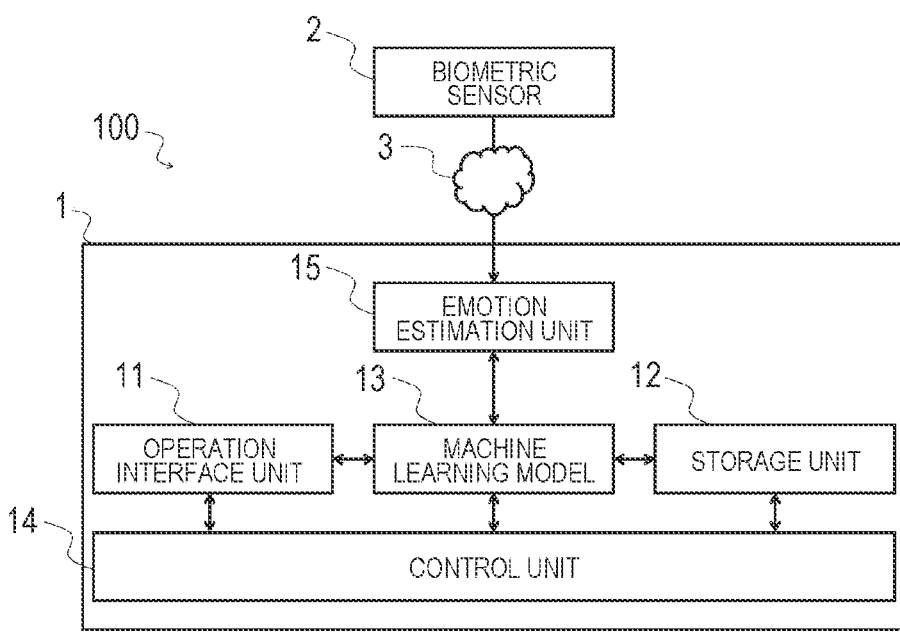
FIG. 5 is a block diagram illustrating a configuration of a content presentation system 100 according to one embodiment of the present technology.

A content presentation system 100 according to one embodiment of the present technology can include a biometric sensor or the like to estimate a current emotion of a user. This will be described with reference to FIG. 5. FIG. 5 is a block diagram illustrating a configuration of the content presentation system 100 according to the one embodiment of the present technology.

As illustrated in FIG. 5, the content presentation system 100 according to the one embodiment of the present technology can further include a biometric sensor 2 and an emotion estimation unit 15. The emotion estimation unit 15 is included in a computer device 1. The biometric sensor 2 and the computer device 1 are connected via an information communication network 3.

The biometric sensor can acquire biometric information related to a user. The biometric information includes, for example, a heart rate, body temperature, blood pressure, blood oxygen concentration, respiration, water, blood glucose, an electrocardiogram, brain waves, and the like.

Conventionally, for example, technology for coding facial actions by image recognition (facial action coding system: FACS, and the like) or technology called affective computing for estimating an emotion on the basis of biometric information such as a lie detector have been used. Similarly, the emotion estimation unit 15 estimates current emotion information indicating a current emotion of a user on the basis of biometric information obtained from sensing information detected by the biometric sensor 2.

Figure 6:
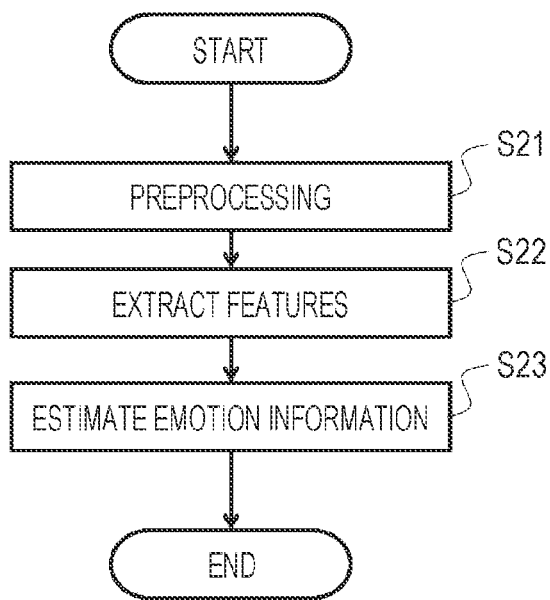
FIG. 6 is a flowchart illustrating an example of a procedure of an emotion estimation unit 15 according to the one embodiment of the present technology.

An example of processing of the emotion estimation unit 15 will be described with reference to FIG. 6. FIG. 6 is a flowchart illustrating the example of a procedure of the emotion estimation unit 15 according to the one embodiment of the present technology.

As illustrated in FIG. 6, first, in step S21, the emotion estimation unit 15 performs preprocessing on sensing information detected by the biometric sensor 2. For example, the emotion estimation unit 15 decomposes the sensing information or removes unnecessary information such as noise.

In step S22, the emotion estimation unit 15 extracts features included in the sensing information to obtain biometric information. These features may be predefined or may be automatically extracted by, for example, deep learning.

In step S23, the emotion estimation unit 15 estimates emotion information on the basis of the biometric information.

In estimating the emotion information, the emotion estimation unit 15 can perform machine learning so as to estimate emotion information suitable for the biometric information on the basis of the biometric information. The emotion estimation unit 15 can be implemented by using, for example, a neural network on which supervised learning is performed. This supervised learning can be performed, for example, by using biometric information as input and emotion information as output.

Although the biometric information of a user has a characteristic depending on the user, according to the present technology, suitable emotion information can be estimated by the characteristic being incorporated.

The emotion estimation unit 15 may perform machine learning so as to estimate emotion information suitable for the biometric information on the basis of biometric information in a case where a user is viewing contents or the like. As a result, the degree of association between the emotion information and the content information is stronger, and content information more suitable for the emotion information is presented.

Furthermore, the emotion estimation unit 15 may use, for example, logistic regression, support vector machine, Bayesian estimation, decision tree, random forest, k-nearest neighbor algorithm, principal component analysis, k-means clustering, or the like.

The current emotion information estimated by the emotion estimation unit 15 is presented in the emotion model illustrated in FIG. 2. As a result, the user can objectively grasp his/her current emotion. As a result, the user can easily select a desired emotion. For example, in a case where a current emotion is a near-lethargic emotion even through the user is at work, the user may select an emotion that enhances concentration.

Figure 7:
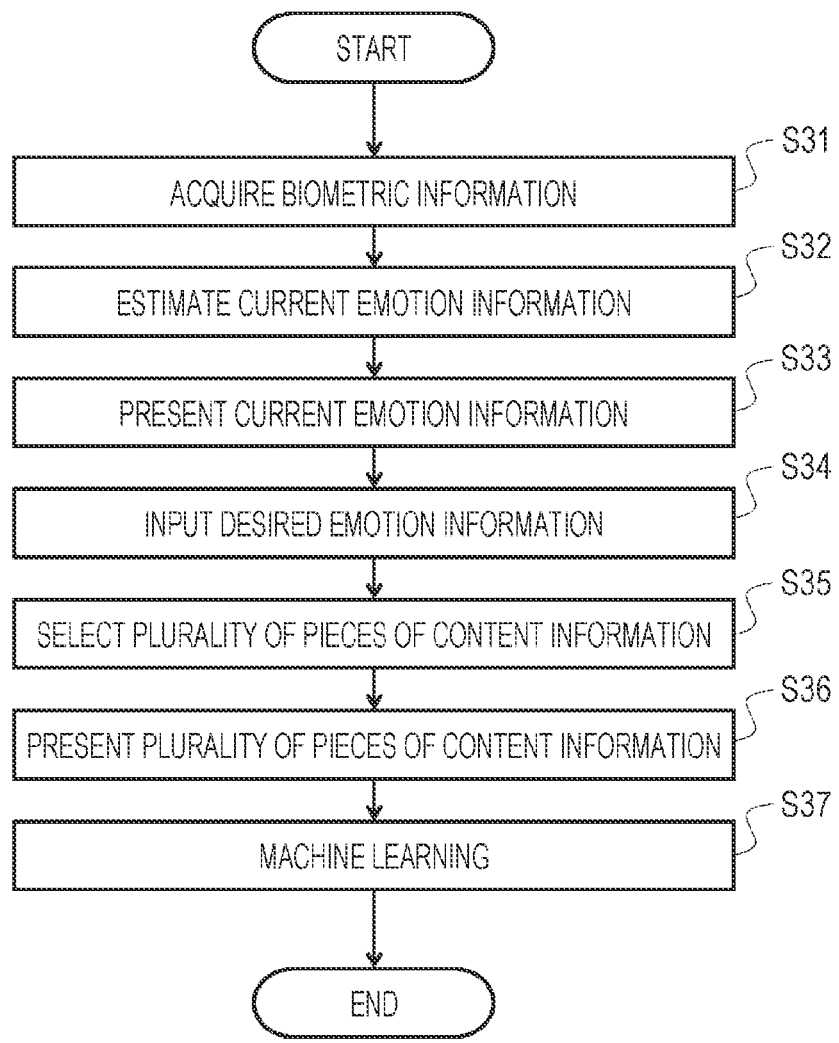
FIG. 7 is a flowchart illustrating an example of a procedure of the content presentation system 100 according to the one embodiment of the present technology.

A procedure of the content presentation system 100 will be described with reference to FIG. 7. FIG. 7 is a flowchart illustrating an example of the procedure of the content presentation system 100 according to the one embodiment of the present technology.

As illustrated in FIG. 7, first, in step S31, the biometric sensor 2 detects sensing information from a user and acquires biometric information.

In step S32, the emotion estimation unit 15 estimates current emotion information related to the user on the basis of the biometric information.

In step S33, the operation interface unit 11 presents the current emotion information to the user.

In step S34, the operation interface unit 11 encourages input of the emotion information desired by the user.

Since the procedure of steps S35 to S37 is similar to that of steps S11 to S13 in FIG. 3, detailed description thereof is omitted.

3. Third Embodiment of Present Technology
(Example 3 of Content Presentation System)

The biometric information obtained in the second embodiment may have different features depending on a context of a user. For example, in a case where a heart rate in a case where a user is sitting is compared with a heart rate in a case where the user is standing, the heart rate in a case where the user is standing tends to be higher. Therefore, in a case where the emotion estimation unit 15 is generated on the basis of biometric information in a case where the user is sitting, an emotion in a case where the user is standing may be erroneously estimated as "nervous". Therefore, biometric information is preferably corrected according to the context of a user.

A content presentation system 100 according to one embodiment of the present technology can include a context sensor or the like to estimate a current context of a user. The context sensor obtains context information indicating information related to a context such as posture or a location of the user. The context information obtains context information such as, for example, whether the user is indoors or outdoors and whether the user is meeting a friend, shopping, walking, or running.

The context sensor can be implemented by using, for example, an angular rate sensor, an acceleration sensor, an inertial measurement unit (IMU), a global positioning system (GPS) positioning unit, a microphone, an ambient light sensor, a schedule management application, or the like. For example, by using an angular rate sensor, an acceleration sensor, an inertial sensor, or the like, context information such as whether the user is walking or walking is obtained. For example, by using a GPS positioning unit, a microphone, an ambient light sensor, or the like, context information such as whether the user is indoors or outdoors is obtained. For example, by using a schedule management application or the like, context information such as whether the user is meeting a friend can be obtained.

Figure 8:
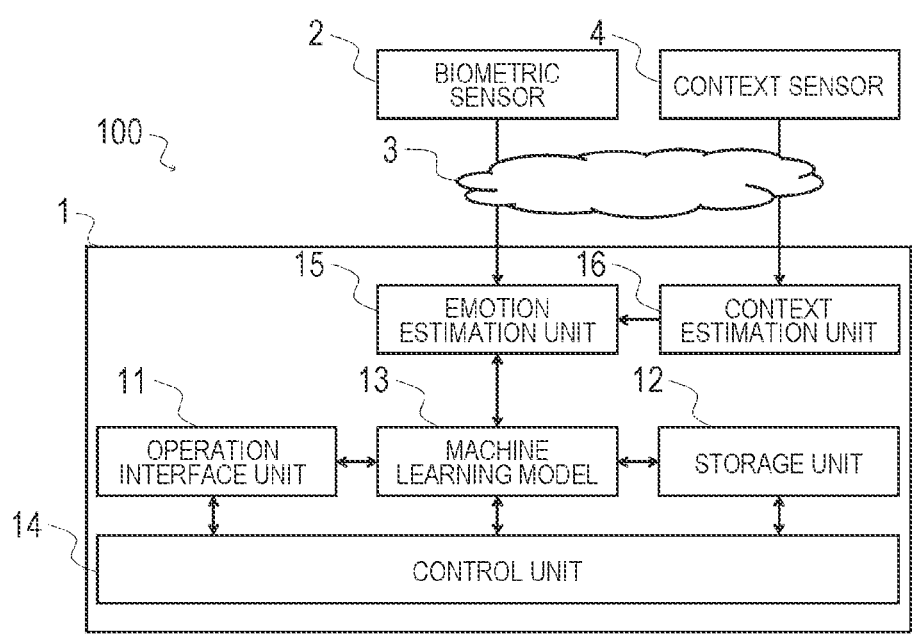
FIG. 8 is a block diagram illustrating a configuration of a content presentation system 100 according to one embodiment of the present technology.

A configuration of the content presentation system 100 according to the one embodiment of the present technology will be described with reference to FIG. 8. FIG. 8 is a block diagram illustrating the configuration of the content presentation system 100 according to the one embodiment of the present technology.

As illustrated in FIG. 8, the content presentation system 100 according to the one embodiment of the present technology can further include a context sensor 4 and a context estimation unit 16. The context estimation unit 16 is included in a computer device 1. The context sensor 4 and the computer device 1 are connected via an information communication network 3.

The context estimation unit 16 estimates context information on the basis of sensing information detected by the context sensor 4.

The context estimation unit 16 can be implemented by using, for example, a neural network on which supervised learning is performed. This supervised learning can be performed, for example, by using sensing information as input and context information as output.

An emotion estimation unit 15 can correct current emotion information on the basis of the context information. Using the example of the heart rate described above, in a case where a heart rate is high because a user is standing, the emotion estimation unit 15 may subtract the heart rate. Alternatively, in a case where the emotion estimation unit 15 is generated, the emotion estimation unit 15 may be generated using the subtracted heart rate as an explanatory variable.

Alternatively, the emotion estimation unit 15 may correct, for example, the intersection X of the coordinate system illustrated in FIG. 2 on the basis of the context information. As a result, for example, the intensity of an emotion or the like is corrected.

Alternatively, the coordinate system and the context information may be associated with each other. For example, a coordinate system in a case where a user is sitting may be different from a coordinate system in a case where the user is standing.

Alternatively, in a case where biometric information before correction is an m-dimensional (for example, three-dimension of a heart rate, a sweat rate, and respiration) vector and context information is an n-dimensional vector, biometric information after the correction may be an m*n-dimensional vector.

Moreover, in estimating emotion information, the emotion estimation unit 15 can perform machine learning so as to estimate emotion information suitable for the biometric information on the basis of content information in addition to the biometric information. The emotion estimation unit 15 can be implemented by using, for example, a neural network on which supervised learning is performed. This supervised learning can be performed, for example, by using biometric information and content information as input and emotion information as output.

Alternatively, the emotion estimation unit 15 may perform machine learning on the basis of a data set in which emotion information and content information for every context are associated with each other.

Although an error occurs in biometric information of a user depending on the context of the user, according to the present technology, suitable emotion information can be estimated by the context being incorporated.

Figure 9:
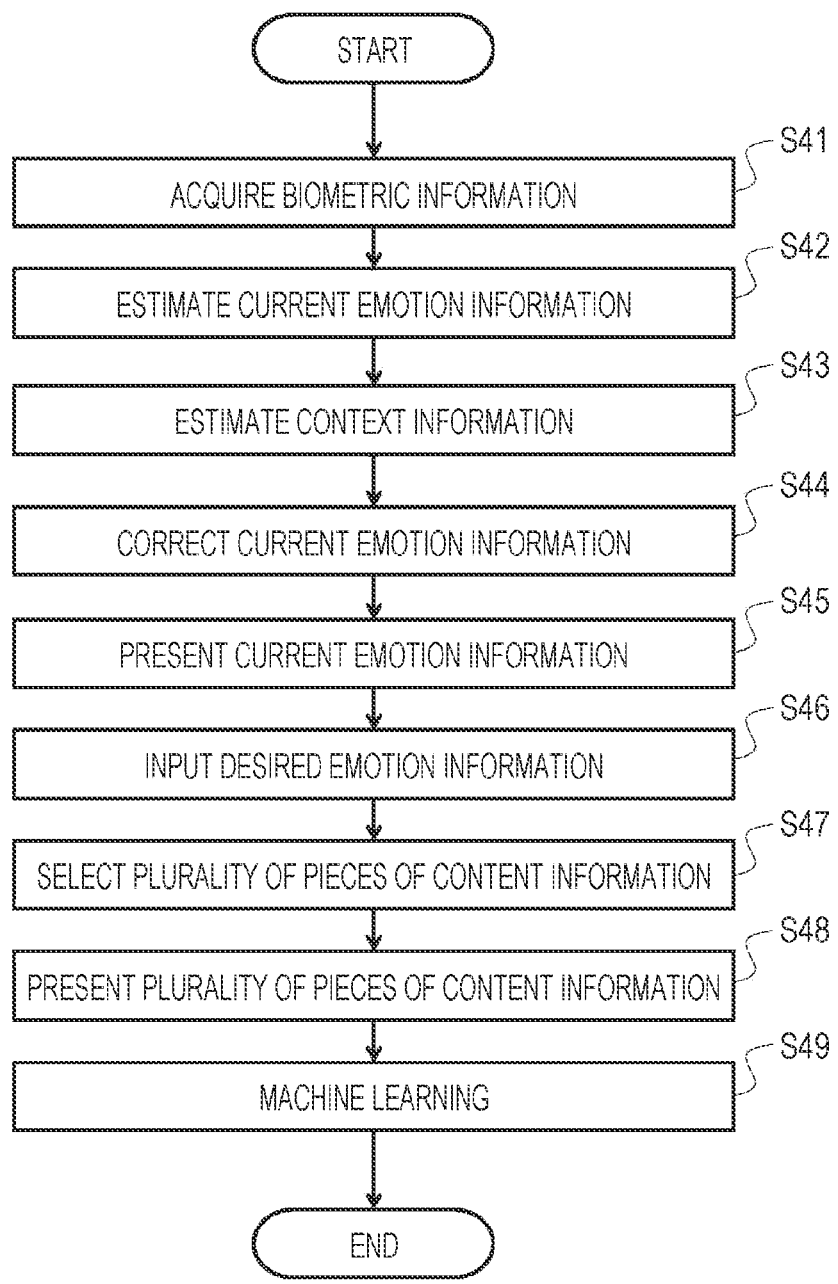
FIG. 9 is a flowchart illustrating an example of a procedure of the content presentation system 100 according to the one embodiment of the present technology.

A procedure of the content presentation system 100 will be described with reference to FIG. 9. FIG. 9 is a flowchart illustrating an example of the procedure of the content presentation system 100 according to the one embodiment of the present technology.

As illustrated in FIG. 9, first, in step S41, a biometric sensor 2 detects sensing information from a user and acquires biometric information.

In step S42, the emotion estimation unit 15 estimates current emotion information related to the user on the basis of the biometric information.

In step S43, the context estimation unit 16 estimates context information on the basis of sensing information detected by the context sensor 4.

In step S44, the emotion estimation unit 15 corrects the current emotion information on the basis of the context information.

Since the procedure of steps S45 to S49 is similar to that of steps S33 to S37 in FIG. 7, detailed description thereof is omitted.

4. Fourth Embodiment of Present Technology
(Example 4 of Content Presentation System)

As an operation interface unit 11 that encourages a user to input desired emotion information, for example, a microphone or a camera may be used, but here, an operation interface unit 11 in a case where a display is used as one embodiment will be described.

Figure 10:
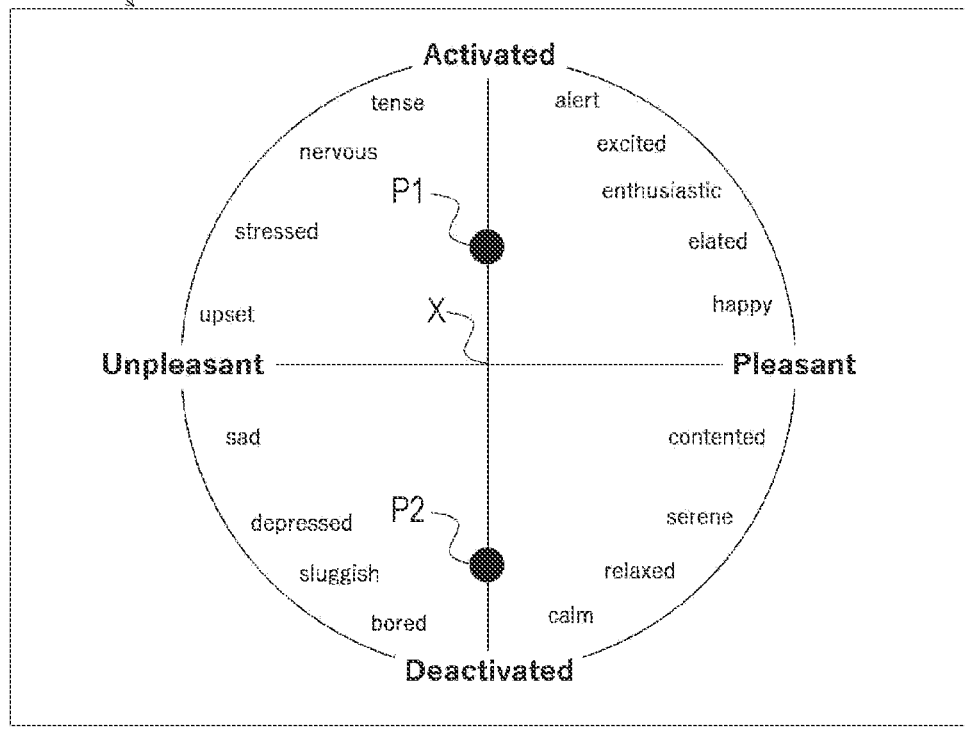
FIG. 10 is a diagram illustrating an example of a screen displayed on an operation interface unit 11 according to one embodiment of the present technology.

An operation method via the operation interface unit 11 will be described with reference to FIG. 10. FIG. 10 is a diagram illustrating an example of a screen displayed on the operation interface unit 11 according to the one embodiment of the present technology. Similarly to FIG. 2, a coordinate system including elements of an emotion as coordinate axes is illustrated.

As illustrated in FIG. 10, current emotion information indicating a current emotion of a user is displayed at a first point P1.

With the first point P1, the user who has objectively recognized the current own emotion can move the first point P1 to a second point P2 indicating desired emotion information. This operation can be performed by a touch operation as long as the operation interface unit 11 includes a touch panel. Alternatively, this operation may be performed by using a mouse. Alternatively, in a case where a head mounted display (HMD) includes the operation interface unit 11, for example, this operation may be performed by an angular rate sensor or the like included in the HMD detecting the angle of the head of the user, or this operation may be performed by the operation interface unit 11 detecting the line-of-sight of the user.

The machine learning model 13 selects a plurality of pieces of content information corresponding to the second point P2.

The operation interface unit 11 presents the plurality of pieces of content information corresponding to the second point P2 selected by the machine learning model 13 to the user. Moreover, the operation interface unit 11 encourages the user to select specific content information from the plurality of pieces of content information.

Here, the fact that a plurality of pieces of content information is selected will be described. The second point P2 indicating desired emotion information is selected in units of millimeters by intuition of the user. Therefore, the position of the second point P2 varies. Therefore, by the plurality of pieces of content information being presented, the influence of this variation is reduced.

Note that a plurality of second points P2 may be selected. At this time, the operation interface unit 11 presents a plurality of pieces of content information corresponding to the plurality of respective second points to a user.

5. Fifth Embodiment of Present Technology
(Example 5 of Content Presentation System)

Subsequently, an operation interface unit 11 in a case where a display is used as one embodiment will be described.

In a case of encouraging input of desired emotion information, the operation interface unit 11 may encourage input of one coordinate, or may encourage continuous or stepwise input of a plurality of coordinates.

Figure 11:
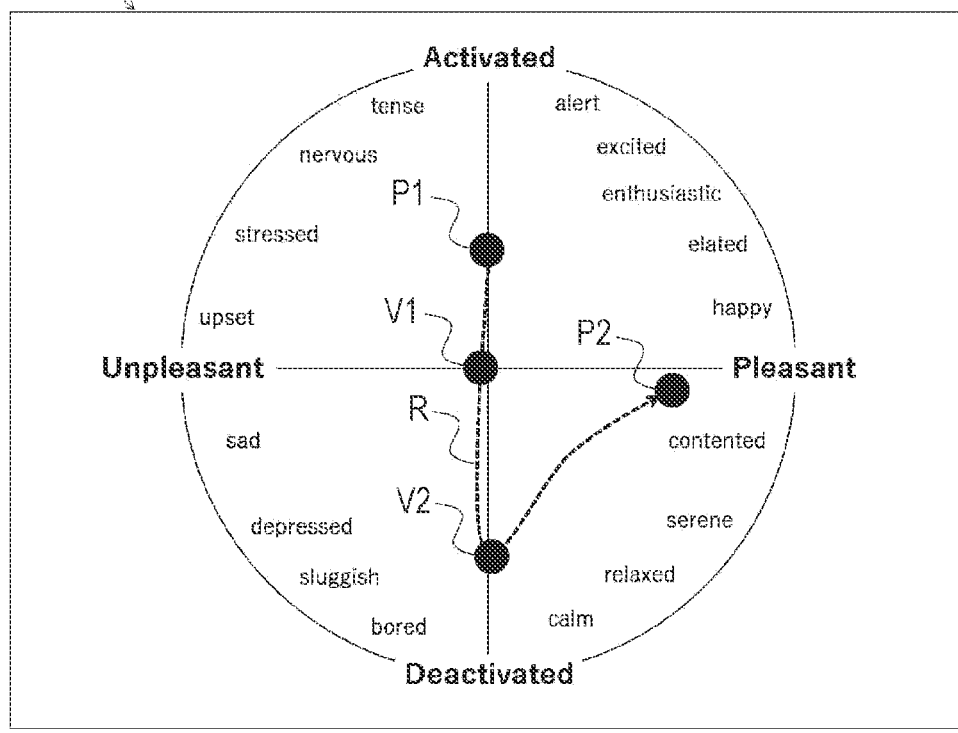
FIG. 11 is a diagram illustrating an example of a screen displayed on an operation interface unit 11 according to one embodiment of the present technology.

An operation method via the operation interface unit 11 will be described with reference to FIG. 11. FIG. 11 is a diagram illustrating an example of a screen displayed on the operation interface unit 11 according to the one embodiment of the present technology.

As illustrated in FIG. 11, a first point P1 is displayed similarly to the fourth embodiment.

With the first point P1, a user who has objectively recognized a current own emotion inputs a route R indicating desired emotion information by moving the first point P1. The route R is formed by continuous or stepwise input of a plurality of coordinates. The user can move the first point P1 to a second point P2 via a first via point V1 and a second via point V2. This operation can be performed by a touch operation or the like similarly to the fourth embodiment.

Note that the number of via points is not limited to two.

The machine learning model 13 selects a plurality of pieces of content information corresponding to one or a plurality of via points included in the route R. In an implementation illustrated in FIG. 11, a plurality of pieces of content information corresponding to the first via point V1 and a plurality of pieces of content information corresponding to the second via point V2 are selected.

The operation interface unit 11 presents the plurality of pieces of content information corresponding to the first via point V1 and the plurality of pieces of content information corresponding to the second via point V2 selected by the machine learning model 13 to the user. Moreover, the operation interface unit 11 encourages the user to select specific content information from the plurality of pieces of content information.

The machine learning model 13, on the basis of the plurality of pieces of content information presented to the user corresponding to predetermined desired emotion information in the route R (first via point V1 and second via point V2 in the present implementation) and content information selected by the user from the plurality of pieces of content information, performs machine learning so as to present the content information suitable for the desired emotion information.

In the fourth embodiment, the user can move from the first point P1 straight to the second point P2. The fourth embodiment is used, for example, in a case where the user wants to immediately feel an emotion indicated at the second point P2.

On the other hand, in this fifth embodiment, the user can move from the first point P1 to the second point P2 while detouring around. The fifth embodiment is used, for example, in a case where the user wants to feel a final emotion while feeling various emotions. In description in which a specific example is used, in a case where a nervous user wants to exert his/her performance, there is a case where the performance can be exerted more by viewing contents by which the user feels relaxed and then viewing contents by which the user feels excited than by immediately viewing contents by which the user feels excited. According to the present technology, content information can be flexibly presented according to the characteristic of the user.

Moreover, the machine learning model 13 may select a plurality of pieces of content information corresponding to the shape of the route R and the second point P2. The machine learning model 13 can select, for example, a plurality of pieces of content information corresponding to the degree of the curve included in the shape.

The operation interface unit 11 presents the plurality of pieces of content information corresponding to the shape of the route R and the second point P2 selected by the machine learning model 13 to the user. Moreover, the operation interface unit 11 encourages the user to select specific content information from the plurality of pieces of content information.

The machine learning model 13, on the basis of the plurality of pieces of content information presented to the user corresponding to the shape of the route R and the second point P2 and content information selected by the user from the plurality of pieces of content information, performs machine learning so as to present the content information suitable for the desired emotion information.

According to the present embodiment, a plurality of pieces of content information presented corresponding to the second point P2 is different between a case of moving from the first point P1 straight to the second point P2 and a case of moving from the first point P1 to the second point P2 while detouring around. Therefore, content information in which the process of changing emotions of a user is considered is presented to the user.

6. Sixth Embodiment of Present Technology
(Content Presentation Device)

Figure 12:
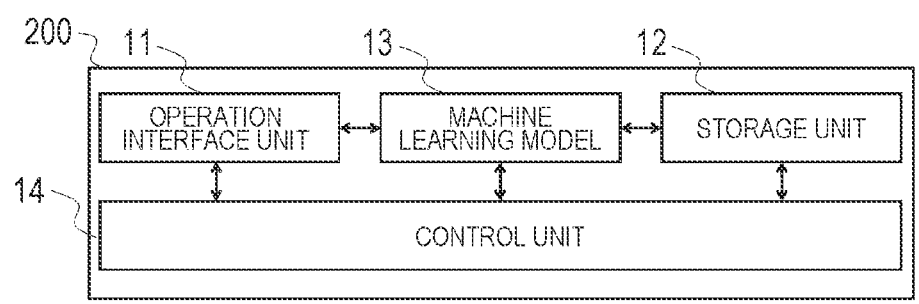
FIG. 12 is a block diagram illustrating a configuration of a content presentation device 200 according to one embodiment of the present technology.

A configuration of a content presentation device according to the first embodiment of the present technology will be described with reference to FIG. 12. FIG. 12 is a block diagram illustrating a configuration of a content presentation device 200 according to one embodiment of the present technology.

As illustrated in FIG. 12, the content presentation device 200 according to the one embodiment of the present technology can include, for example, an operation interface unit 11, a storage unit 12, a machine learning model 13, and a control unit 14.

The machine learning model 13 performs machine learning so as to present content information suitable for emotion information. More specifically, the machine learning model 13, on the basis of a plurality of pieces of content information presented to a user corresponding to the emotion information and content information selected by the user from the plurality of pieces of content information, performs machine learning so as to present the content information suitable for the emotion information.

For the content presentation device 200, the technology related to the content presentation system 100 described above may be used. Therefore, repeated description of the operation interface unit 11, the storage unit 12, the machine learning model 13, and the control unit 14 is omitted.

7. Seventh Embodiment of Present Technology (Content Presentation Method)

A content presentation method according to one embodiment of the present technology includes a computer device that holds content information associated with emotion information indicating an emotion of a user.

Figure 13:
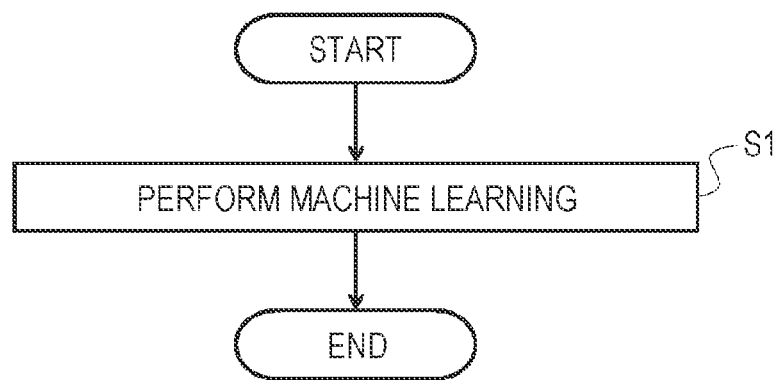
FIG. 13 is a flowchart illustrating an example of a procedure of a content presentation method according to one embodiment of the present technology.

A procedure of the content presentation method according to the one embodiment of the present technology will be described with reference to FIG. 13. FIG. 13 is a flowchart illustrating an example of the procedure of the content presentation method according to the one embodiment of the present technology.

As illustrated in FIG. 13, the content presentation method according to the present embodiment at least includes, on the basis of a plurality of pieces of content information presented to the user corresponding to desired emotion information indicating emotion information desired by the user and content information selected by the user from the plurality of pieces of content information, performing machine learning so as to present the content information suitable for the emotion information by the computer device (step S1).

In the content presentation method according to the present embodiment, the technology according to another embodiment described above may be used. Therefore, repeated description of the technology described in the embodiments described above is omitted.

The content presentation method according to the present embodiment can be implemented by using software and hardware. Specifically, for example, a CPU included in hardware reads a program for implementing the content presentation method according to the present embodiment, whereby the content presentation method according to the present embodiment can be implemented.

In addition to this, the configurations described in the embodiments described above can be selected or changed as appropriate to other configurations without departing from the gist of the present technology.

Note that the effects described in the present specification are merely examples and are not limited thereto, and other effects may be provided.

Note that the present technology can also have the following configurations.

[1]
A content presentation system including a computer device that holds content information associated with emotion information indicating an emotion of a user,
in which the computer device at least includes a machine learning model that, on the basis of a plurality of pieces of content information presented to the user corresponding to desired emotion information indicating emotion information desired by the user and content information selected by the user from the plurality of pieces of content information, performs machine learning so as to present the content information suitable for the emotion information.

[2]
The content presentation system according to [1],
in which the emotion information and the content information are associated with each other on the basis of a coordinate system having elements of the emotion as coordinate axes.

[3]
The content presentation system according to [2],
in which the coordinate system is a Russell's circumplex model.

[4]
The content presentation system according to any one of [1] to [3],
in which current emotion information indicating the emotion that is current of the user is estimated on the basis of biometric information obtained from sensing information detected by a biometric sensor.

[5]
The content presentation system according to [4],
in which the current emotion information is corrected on the basis of context information related to a context of the user obtained from sensing information detected by a context sensor.

[6]
The content presentation system according to [4] or [5] further including an emotion estimation unit,
in which the emotion estimation unit that performs machine learning so as to estimate the emotion information suitable for the biometric information on the basis of the biometric information.

[7]
The content presentation system according to any one of [1] to [6] further including an operation interface unit,
in which the operation interface unit encourages input of the desired emotion information.

[8]
The content presentation system according to [7],
in which the operation interface unit presents the content information corresponding to the desired emotion information and/or encourages selection of the content information.

[9]
The content presentation system according to [7] or [8],
in which the operation interface unit encourages continuous or stepwise input of the desired emotion information, and
the machine learning model, on the basis of a plurality of pieces of the content information presented to the user corresponding to the desired emotion information that is predetermined in a route formed by the input and content information selected by the user from the plurality of pieces of content information, performs machine learning so as to present the content information suitable for the desired emotion information.

[10]
The content presentation system according to any one of [7] to [9],
in which the operation interface unit encourages continuous or stepwise input of the desired emotion information, and
the machine learning model, on the basis of a plurality of pieces of the content information presented to the user corresponding to a shape of a route formed by the input and the desired emotion information and content information selected by the user from the plurality of pieces of content information, performs machine learning so as to present the content information suitable for the desired emotion information.

[11]

A content presentation device that holds content information associated with emotion information indicating an emotion of a user, the content presentation device at least including a machine learning model that, on the basis of a plurality of pieces of content information presented to the user corresponding to desired emotion information indicating emotion information desired by the user and content information selected by the user from the plurality of pieces of content information, performs machine learning so as to present the content information suitable for the emotion information.

[12]

A content presentation method including a computer device that holds content information associated with emotion information indicating an emotion of a user, the content presentation method at least including, on the basis of a plurality of pieces of content information presented to the user corresponding to desired emotion information indicating emotion information desired by the user and content information selected by the user from the plurality of pieces of content information, performing machine learning so as to present the content information suitable for the emotion information by the computer device.

REFERENCE SIGNS LIST

100 Content presentation system
1 Computer device
11 Operation interface unit
12 Storage unit
13 Machine learning model
14 Control unit
15 Emotion estimation unit
16 Context estimation unit
2 Biometric sensor
3 Information communication network
4 Context sensor
P1 First point
P2 Second point
R Route
V1 First via point
V2 Second via point
200 Content presentation device
S1 Machine learning

The invention claimed is:

1. A content presentation system comprising:
a computer device that holds content information associated with emotion information indicating an emotion of a user; and
an operation interface unit,
wherein the operation interface unit encourages continuous or stepwise input of desired emotion information, and wherein the computer device at least includes a machine learning model that, on a basis of a plurality of pieces of content information presented to the user corresponding to the desired emotion information that is predetermined in a route formed by the continuous or stepwise input and content information selected by the user from the plurality of pieces of content information presented to the user, performs machine learning to present content information suitable for the desired emotion information.

2. The content presentation system according to claim 1, wherein the emotion information and the content information are associated with each other on a basis of a coordinate system having elements of the emotion as coordinate axes.

3. The content presentation system according to claim 2, wherein the coordinate system is a Russell's circumplex model.

4. The content presentation system according to claim 1, wherein current emotion information indicating the user's current emotion is estimated on a basis of biometric information obtained from sensing information detected by a biometric sensor.

5. The content presentation system according to claim 4, wherein the current emotion information is corrected on a basis of context information related to a context of the user obtained from sensing information detected by a context sensor.

6. The content presentation system according to claim 4 further comprising an emotion estimation unit,
wherein the emotion estimation unit performs machine learning as to estimate the current emotion information.

7. The content presentation system according to claim 1, wherein the operation interface unit presents the content information corresponding to the desired emotion information and/or encourages selection of the content information.

8. A content presentation device that holds content information associated with emotion information indicating an emotion of a user, the content presentation device at least comprising:
an operation interface unit, wherein the operation interface unit encourages continuous or stepwise input of desired emotion information; and
a machine learning model that, on a basis of a plurality of pieces of content information presented to the user corresponding to a shape of a route formed by the continuous or stepwise input, the desired emotion information, and content information selected by the user from the plurality of pieces of content information presented to the user, performs machine learning to present content information suitable for the desired emotion information.

9. A content presentation method comprising a computer device that holds content information associated with emotion information indicating an emotion of a user, the content presentation method at least comprising:
receiving continuous or stepwise input of desired emotion information; and
on a basis of a plurality of pieces of content information presented to the user corresponding to a shape of a route formed by the continuous or stepwise input, the desired emotion information, and content information selected by the user from the plurality of pieces of content information presented to the user, performing machine learning to present content information suitable for the desired emotion information by the computer device.

* * * * *